United States Patent [19]
Folsom, Jr. et al.

[11] Patent Number: 6,102,702
[45] Date of Patent: Aug. 15, 2000

[54] QUICK TIGHTENING ABUTMENT LOCK

[75] Inventors: Aubrey Clinton Folsom, Jr., 7191 Deer Mountain Cir., Pelham, Ala. 35214; Craig Estes, Birmingham, Ala.

[73] Assignee: Aubrey Clinton Folsom, Jr., Birmingham, Ala.

[21] Appl. No.: 09/221,737

[22] Filed: Dec. 28, 1998

[51] Int. Cl.$^7$ ...................................................... A61C 8/00
[52] U.S. Cl. ............................................. 433/172; 433/173
[58] Field of Search ..................................... 433/172, 173, 433/174, 175, 176; 606/60, 62, 63

[56] References Cited

U.S. PATENT DOCUMENTS

| | | | |
|---|---|---|---|
| 5,468,150 | 11/1995 | Brammann | 433/173 |
| 5,470,230 | 11/1995 | Daftary et al. | 433/173 |
| 5,823,776 | 10/1998 | Duerr et al. | 433/173 |

*Primary Examiner*—John J. Wilson
*Attorney, Agent, or Firm*—Robert J. Veal; Chris A. Holland; Burr & Froman, LLP

[57] ABSTRACT

An abutment lock utilized with an implant anchor which has a substantially smooth axial bore which may have longitudinal guide grooves formed therein. The abutment element has an insertion end which is also substantially smooth and which terminates in an oblique lower surface. A bore through the abutment allows a threaded bolt to engage a wedge nut having a cooperatively formed oblique surface and a plurality of guide protrusions such that rotation of the bolt urges the nut against the abutment oblique surfaces thereby urging the smooth surfaces of the nut and abutment into intimate surface to surface contact with the cylindrical wall of the anchor. The relatively large surface area in compressive contact between the abutment and the anchor resists movement between the components.

25 Claims, 6 Drawing Sheets

QUICK TIGHTENING ABUTMENT LOCK

FIELD OF THE INVENTION

The present invention relates to medical implants and more particularly to implants wherein the implant includes an anchor which is osseointegrated into the mandible or maxilla to replace a natural tooth root. The implant anchor supports an abutment which in turn supports a prosthetic tooth or other fixture. In greater particularity the present invention relates to the internal structure of the anchor and the abutment connector to the prosthesis.

BACKGROUND OF THE INVENTION

The medical implant industry spans a variety of disciplines, drawing from the biological sciences for materials that are compatible with living organisms, from the metallurgical sciences for materials that can withstand the stresses encountered in biological functions without excessive deterioration, from the machine tool sciences for the fabrication techniques necessary to make the devices from the selected materials for the specific application. Accordingly, the art includes miniature fixtures and threaded members as well as devices designed to replace or assist the larger bones of the body. In each of these cases a continual concern is intermodular connectivity which is critical to acceptance of the biological implant as a viable alternative for more than the most extreme cases. That is to say, a patient with no options but for the use of a medical implant may be willing to suffer secondary surgical procedures when the implant components loosen from one another; however, the pain, expense, and inconvenience of such repeated surgical procedures reduces the acceptance of the procedures among many who would potentially benefit therefrom.

Accordingly a persistent need exists for implant technology which provides the assurance of tight seals between components and which can be manipulated with relative ease and minimal trauma to the patient to effect repair or maintenance.

SUMMARY OF THE INVENTION

It is the object of the present invention to provide a releasable connection between the medical implant and the prosthesis abutment inserted thereinto such that maintenance and repair of the prosthetic components may be facilitated.

It is a further object of the invention to simplify the placement of abutments into the previously implanted anchors of medical implants.

Yet another object of the invention is to simplify the manufacture of such abutments and implant components.

These and other objects and advantages are accomplished in my invention through the use of a novel locking mechanism relative to the implant components. Specifically, the implant anchor of my invention utilizes a substantially smooth axial bore which may have longitudinal guide grooves formed therein. The abutment element has an insertion end which is also substantially smooth and which terminates in an oblique lower surface. A bore through the abutment allows a threaded bolt to engage a wedge nut having a cooperatively formed oblique surface and a plurality of guide protrusions such that rotation of the bolt urges the nut against the abutment oblique surfaces thereby urging the smooth surfaces of the nut and abutment into intimate surface to surface contact with the cylindrical wall of the anchor.

BRIEF DESCRIPTION OF THE DRAWINGS

Apparatus embodying features of the present invention are depicted in the drawings appended hereto which form a portion of this disclosure and wherein.

DESCRIPTION OF A PREFERRED EMBODIMENT

Figure 1:
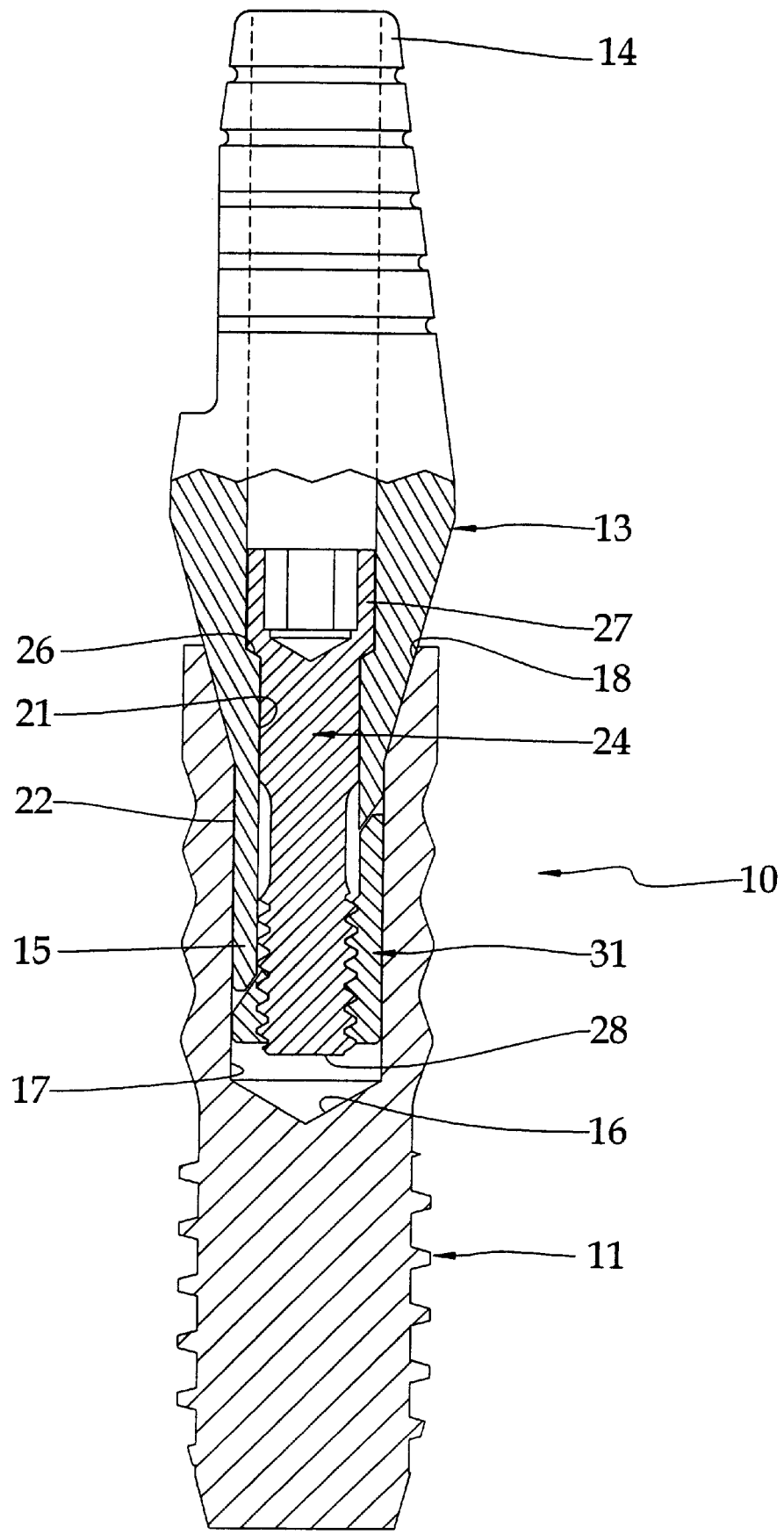
FIG. 1 is a sectional view along a longitudinal axis of an implant assembly.
Figure 4:
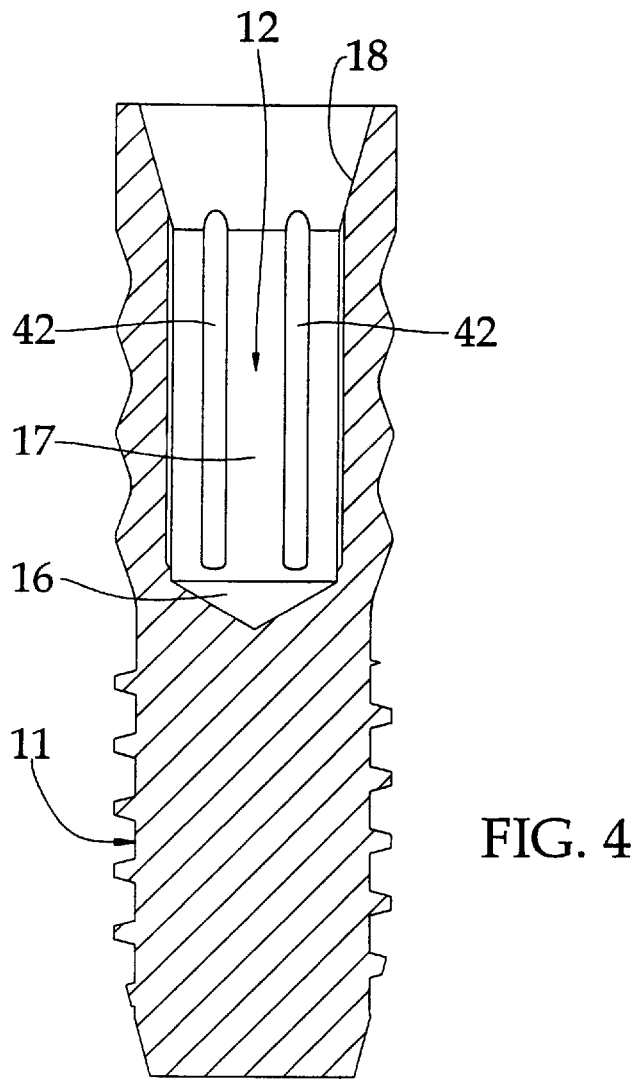
FIG. 4 is a sectional view of the implant anchor.

Referring to the drawings for a clearer understanding of the invention it may be seen in FIG. 1 that my invention is an improvement to medical implants wherein the implant assembly 10 comprises an implant anchor 11, preferably having an external configuration similar to that disclosed and claimed in my copending application Ser. No. 08/762,881, now U.S. Pat. No. 5,782,918 which is incorporated herein by reference for all purposes. Internally, my improved assembly utilizes a performed bore 12, as shown in FIG. 4, in the anchor 11 to receive and maintain an abutment 13. Bore 12 includes a terminal region 16 within anchor 11, including a smooth substantially cylindrical wall 17 circumscribing said terminal region and a generally conic entrant region 18 tapering to cylindrical wall 17 at a coronal end of anchor 11.

Abutment 13 includes a superior end 14 for receiving a prosthesis, such as a dental prosthesis thereon and an insertion end 15 adapted for insertion into bore 12 at the coronal end of anchor 11. It will be noted that abutment 13 has a smooth internal bore 21 and substantially smooth outer walls 22 at insertion end 15. Bore 21 has an increased diameter at the superior end of abutment 13 such that a laterally extending seat 26 is formed in said abutment internal bore. Insertion end 15 terminates at an oblique bearing surface 23 formed transversely of internal bore 21. A lock bolt 24 having a head 27 and threaded distal end 28 is freely rotatable within bore 21 with seat 26 acting as a stop and bearing surface for bolt head 27.

Threadedly engaged on distal end 28 is a locking element 31 which secures abutment 13 to anchor 11 as bolt 24 is rotated to urge locking element 31 between oblique bearing surface 23 and cylindrical wall 17. Locking element 31 is a wedge nut internally threaded as at 33 and dimensioned to fit snugly within axial bore 12, such that rotation of bolt 24 urges wedge nut 31 axially within axial bore 12.

Figure 2:
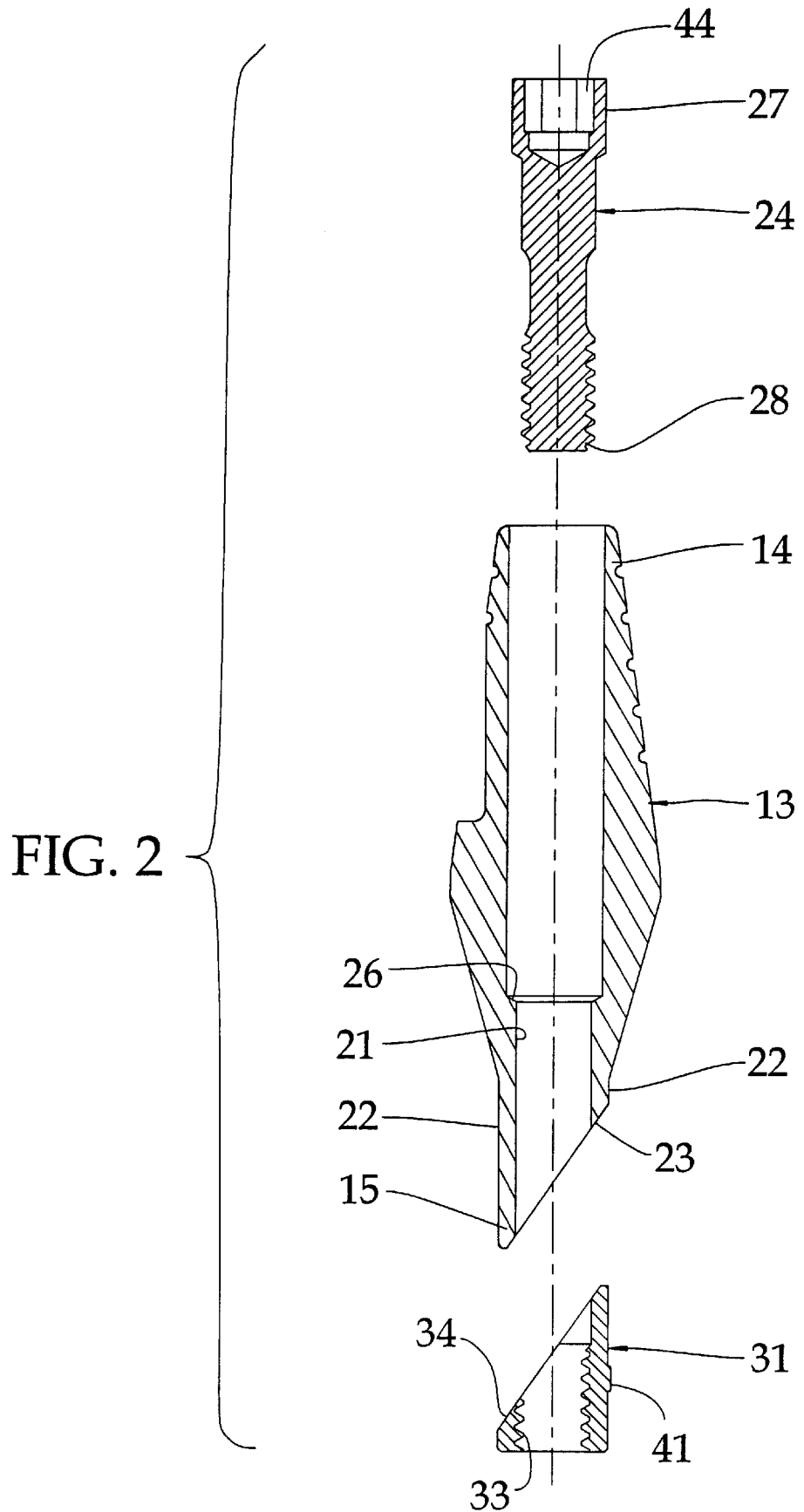
FIG. 2 is an exploded sectional view of an implant lock.
Figure 6:
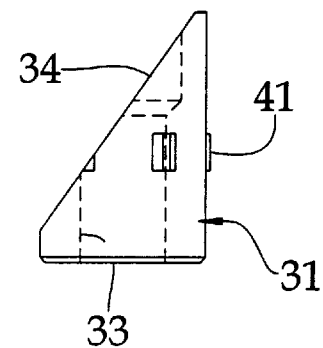
FIG. 6 is an elevational view of the abutment lock.

Wedge nut 31 includes a bearing surface 34 as shown in FIG. 6, formed obliquely to bolt 24 for confronting engagement with oblique bearing surface 23 (FIG. 2) of abutment 13 such that rotation of bolt 24 urges wedge nut 31 and abutment 13 into alignment along the mating oblique bearing surfaces 23 and 34. As the oblique surfaces align and the further rotation of the bolt 24 tightens the connection a component of the force applied in rotation of bolt 24 is transferred laterally to urge wedge nut 31 and abutment insertion end 15 laterally against cylindrical wall 17. As will be appreciated the oblique surfaces will create a greater or lesser force normal to wall 17 depending on the angle of the surface relative to the axis of rotation; however, in this application an angle of about 35° is acceptable.

Figure 3:
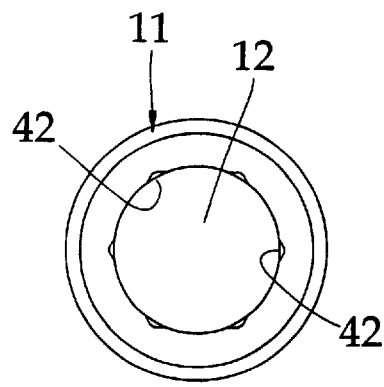
FIG. 3 is a plan view of the implant anchor.
Figure 5:
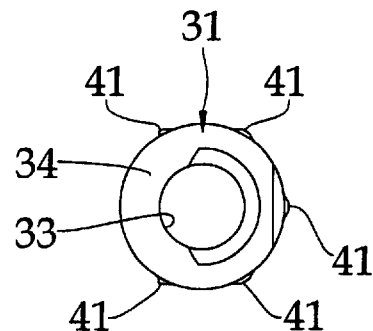
FIG. 5 is a plan view of the abutment lock.

As may be seen in FIGS. 3 to 5, wedge nut 31 has a plurality of angularly spaced protrusions 41 formed thereon for engagement in selected one of a plurality of indexing grooves 42 formed in wall 17 of axial bore 12. Protrusions 41 are guides to maintain the wedge nut and abutment in a preselected angular alignment relative to the implant anchor 11; therefore, the height of the protrusions is less than the depth of the grooves such that the outer surface of wedge nut 31 bears fully against cylindrical wall 17 when the bolt 24 is rotated to secure the abutment 13 in the anchor 11.

To facilitate the tightening of the components, head 27 is provided with a socket or other drive element 44 such that a tool may be used to insert with in the bore 21 and rotate bolt 24. Specifically it is contemplated that a small socket for accommodating a hex type wrench is formed in head 27 and allows the dentist to tighten or loosen bolt 24 as required.

It may be seen that when the wedge nut is fully seated between the abutment and cylindrical bore of the anchor that the smooth surfaces of the abutment, nut, and anchor are held in compression over a relatively large area, thereby providing substantial resistance to relative movement in any direction.

In operation, the anchor 11 is inserted into a formed hole in the osseous structure of the jaw and allowed to heal, with the osseous structure integrating the anchor thereinto. After healing has occurred the abutment 13 with the lock nut 31 connected thereto by bolt 24 is inserted into bore 12 and properly angularly positioned within a selected set of grooves 42. Thereafter a suitable tool is used to engage the head of bolt 24 and rotate the bolt to draw the nut 31 up against oblique surface 23 such that the mating transverse surfaces transfer the locking forces transversely, i.e., the components are urged laterally thereby wedging securely within bore 12. To release the abutment, the dentist can reverse the rotation of the bolt, thereby releasing the wedging forces between the abutment and wedge nut.

Figure 7:
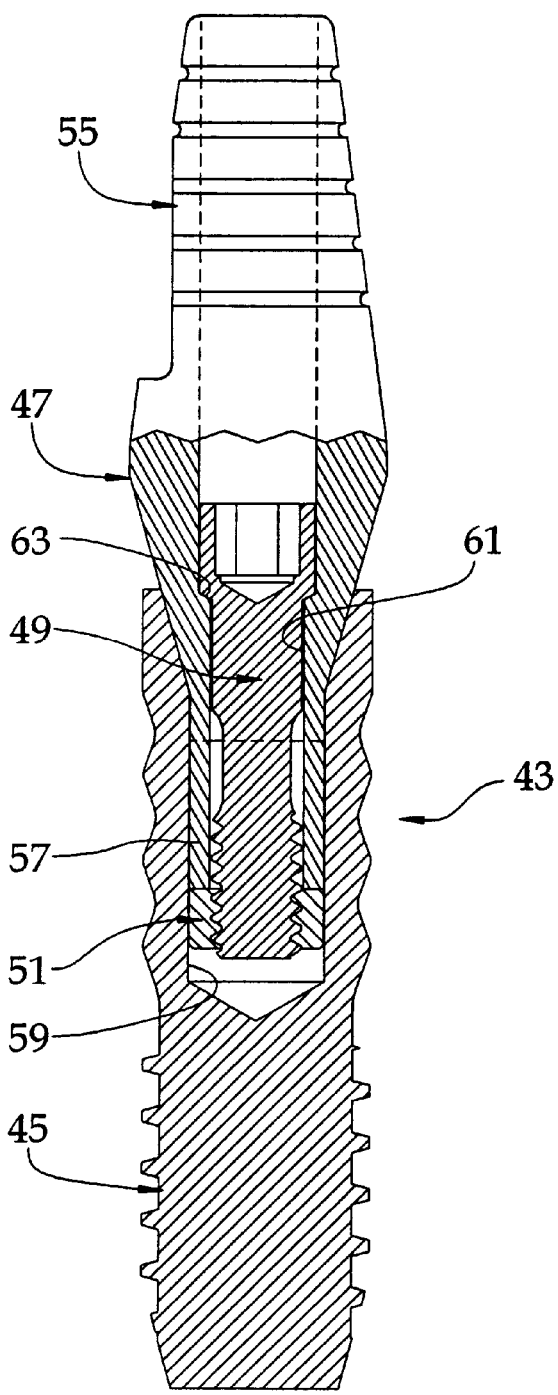
FIG. 7 is a sectional view along a longitudinal axis of an implant assembly.
Figure 8:
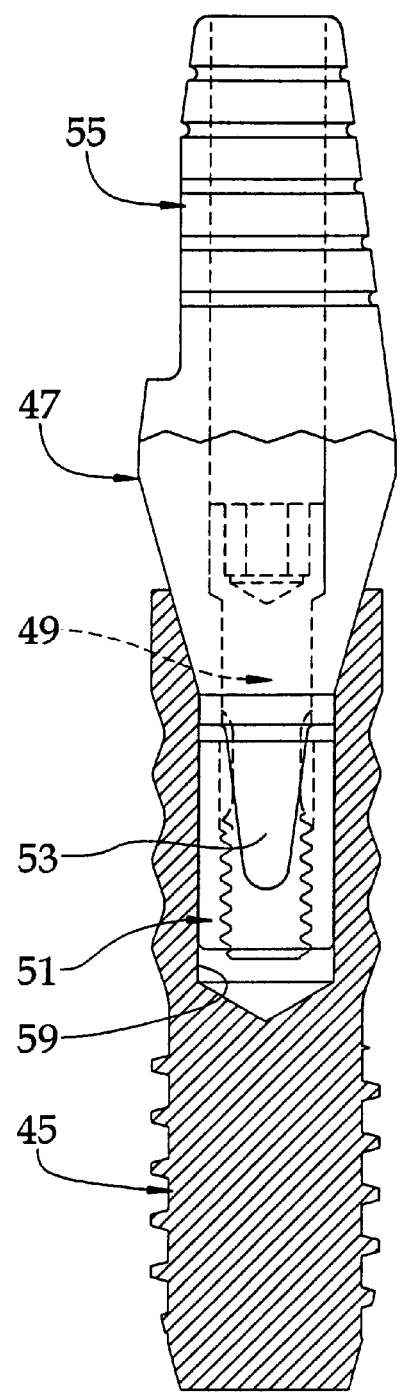
FIG. 8 is a sectional view along a longitudinal axis of an implant assembly rotated ninety degrees.

An alternative embodiment of the invention may be seen by viewing FIG. 7. FIG. 7 represents again the basic implant structure 43 comprising an anchor 45, an abutment 47, a screw 49 and a locking element 51.

Figure 9:
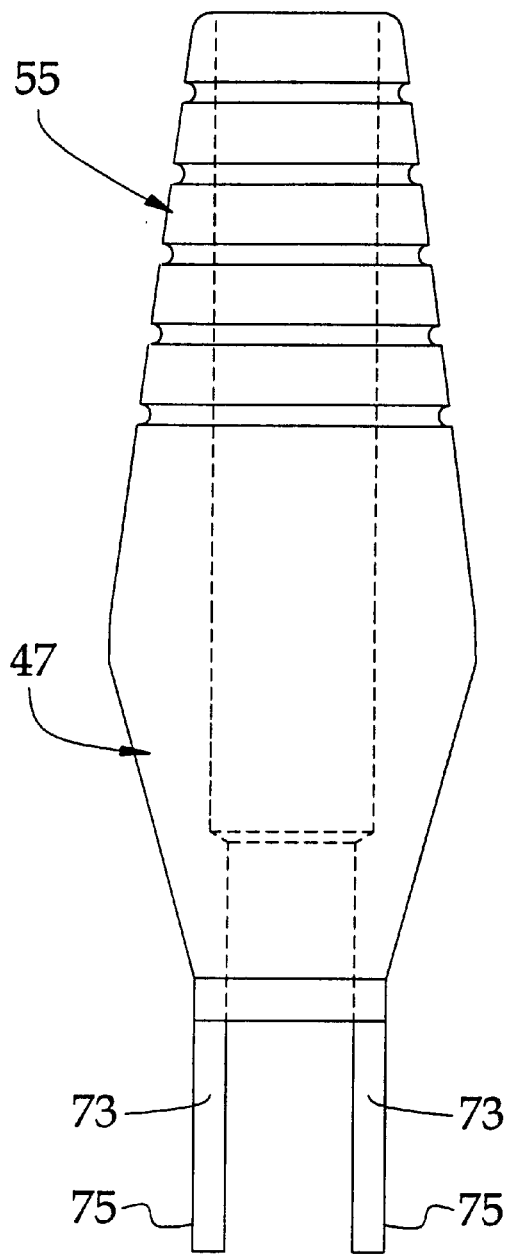
FIG. 9 is a plan view of the abutment.
Figure 10:
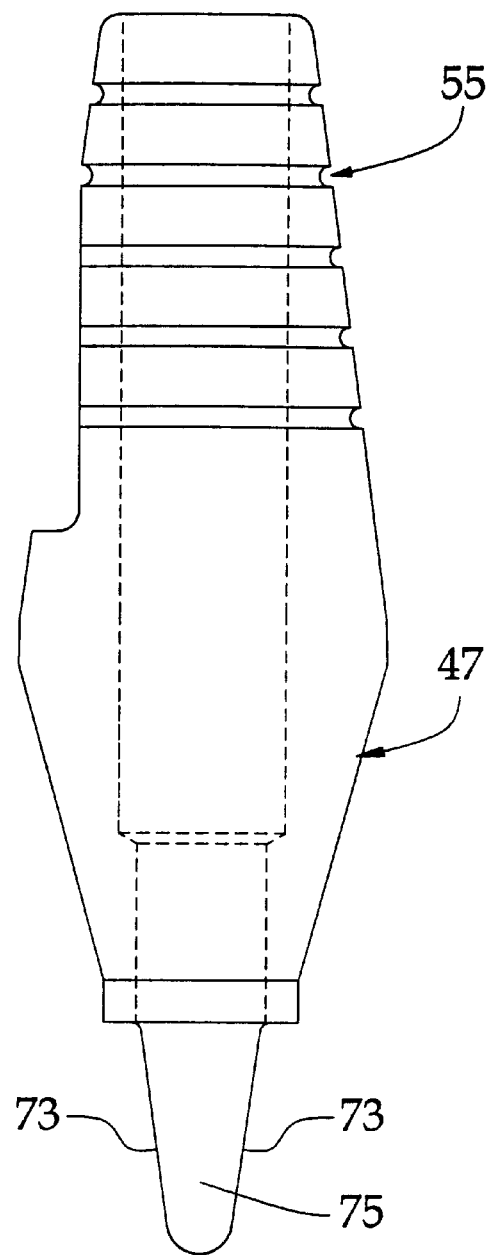
FIG. 10 is an elevational view of the abutment lock.

Unlike the abutment 13 depicted in FIG. 1, abutment 47 includes a superior end 55 for receiving a prosthesis, such as a dental prosthesis thereon and an insertion end 57 for insertion into bore 59 at the coronal end of anchor 45. Abutment 47 has a smooth internal bore 61 that extends from the superior end 55 to a laterally extending seat 63. The smooth internal bore continues to the insertion end 57 with a decreased diameter extending from the lateral seat 63. Insertion end 57 terminates with two triangular-shaped parallel prongs 75 as depicted in FIG. 9 having four (4) oblique bearing surfaces 73 formed transversely of internal bore 61 as depicted in FIG. 10.

Figure 11:
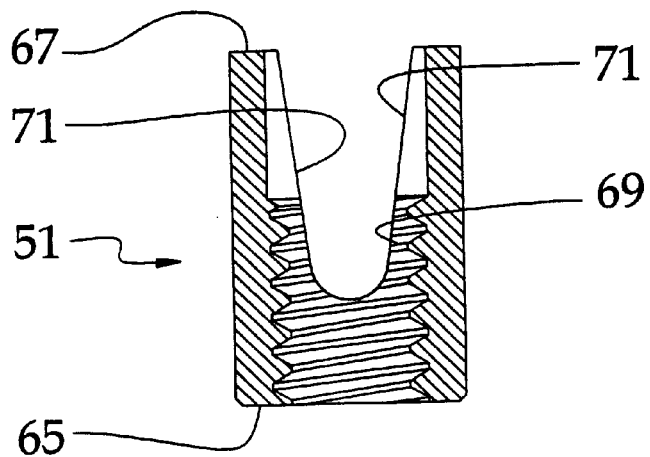
FIG. 11 is an elevational view of the abutment lock.
Figure 12:
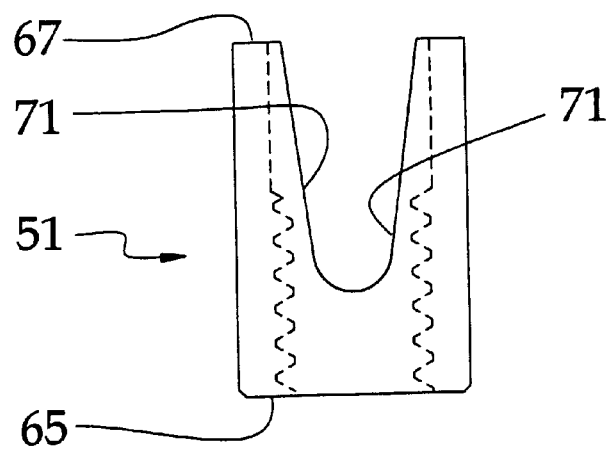
FIG. 12 is an elevational view of the abutment lock.
Figure 13:
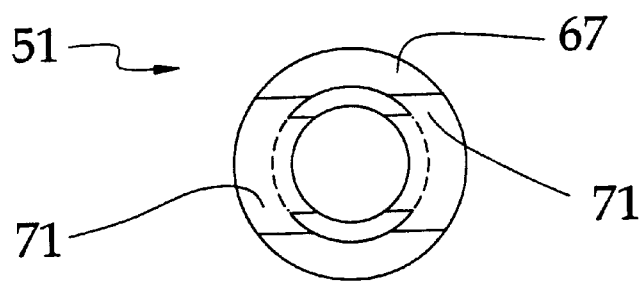
FIG. 13 is a plan view of the abutment lock.

FIG. 11 depicts the cylindrical locking element 51 which is situated in the distal end of the internal bore of anchor 45. The locking element is a cylindrical wedge nut 51 having an insertion end 65, a superior end 67 and a partially threaded internal bore 69. The superior end 67 has two triangular slits opening at the superior end 67 and tapering therefrom.

The locking element 51 secures the abutment 47 to anchor 45 as bolt 49 is rotated to axially urge locking element 51 with the two triangular prongs 45 toward the insertion end 57 of the abutment 47. Urging the wedge nut and the triangular prongs of the abutment together causes the wedge nut to expand as the oblique surfaces 73 of the prongs 75 and the slits 71 engage. As the nut expands, the outer surface contacts the smooth axial bore 59 of the anchor and secures the wedge nut abutment combination thereto. Further tightening of the screw member 49 increases the expansion force applied and increases the force applied to the surface of axial bore 59.

It is to be understood that the form of the invention shown is a preferred embodiment thereof and that various changes and modifications may be made therein without departing from the spirit of the invention or scope as defined in the following claims.

What is claimed is:

1. In an implant system for attaching prosthetic devices to the osseous structure of the body wherein an implant anchor is osseointegrated into the bone of a patient in a preprepared hole, the combination therewith comprising:

a. an implant anchor having an axial bore which is divided into a plurality of regions including a terminal region within said anchor, including a smooth substantially cylindrical wall circumscribing said terminal region and a generally cylindrical entrant region circumscribing the bore at a coronal end of said anchor;

b. an abutment for connecting a prosthesis to said anchor and having an insertion end adapted for insertion into said bore at said coronal end of said anchor, said abutment having an internal bore and smooth outer walls at said insertion end and an oblique bearing surface formed transversely of said internal bore at insertion end; and, c. means for connecting said abutment to said anchor by urging a locking element between said oblique bearing surface and said cylindrical wall.

2. The combination as defined in claim 1 wherein said means for connecting comprises a threaded member extending through said internal bore and threadedly engaging a wedge nut within said axial bore, such that rotation of said threaded member urges said wedge nut axially within said axial bore.

3. The combination as defined in claim 2 wherein said wedge nut includes a bearing surface formed obliquely to said threaded member for confronting engagement with said oblique bearing surface of said abutment such that rotation of said threaded member urges said wedge nut against said oblique bearing surface such that a component of the force applied in rotation of said threaded member is transferred to urge said nut and abutment insertion end laterally against said cylindrical walls.

4. The combination as defined in claim 3 wherein said threaded member has a laterally extending shoulder for engagement with a laterally extending seat formed in said abutment internal bore.

5. The combination as defined in claim 3 wherein said oblique bearing surface and said smooth outer wall define an included angle of about 35° at said insertion end.

6. The combination as defined in claim 3 wherein said threaded member includes means formed on an upper end thereof for engagement by a selected tool to impart rotation to said threaded member.

7. The combination as defined in claim 6 wherein said means for engagement comprises a drive socket formed in said threaded member.

8. The combination as defined in claim 6 wherein said means for engagement comprises a drive head formed on said threaded member.

9. The combination as defined in claim 3 wherein said wedge nut has a smooth outer wall such that maximum surface to surface contact is made between said wedge nut and said wall of said axial bore.

10. The combination as defined in claim 3 wherein said wedge nut has a plurality of angularly space protrusions formed thereon for engagement in selected one of a plurality of indexing grooves formed in said wall of said axial bore.

11. Apparatus for attaching a prosthesis to living tissue, comprising in combination, a. anchor means, having a generally longitudinally formed receptacle therein, insertable into a cavity formed in living bone tissue for osseointegration thereinto as an anchor for a prosthesis; and, b. abutment means for connecting said anchor means to said prosthesis having a portion thereof insertable into said receptacle; and, c. lock means for engaging said receptacle and said abutment such that said abutment is urged transversely of said longitudinal receptacle in locking engagement.

12. Apparatus as defined in claim 11 wherein said receptacle is defined by a generally cylindrical wall extending from a receptacle opening at a coronal end of said anchor means.

13. Apparatus as defined in claim 12 wherein said abutment means comprises a unitary member having an insertion end for inserting said abutment into said bore of said anchor means, an internal bore and a receiving end, said insertion end comprising an oblique bearing surface having one or more symmetrical protrusions.

14. Apparatus as defined in claim 13 wherein said locking means comprises a wedge nut and a longitudinally oriented screw, said wedge nut having a terminal end, a threaded cylindrical bore and a receiving end, said receiving end having a bearing surface complimentary to said bearing surface of said abutment such that said receiving end of said wedge nut and said insertion end of said abutment abut along said bearing surface.

15. Apparatus as defined in claim 14 wherein said screw extends through said internal bore of said abutment engaging at said receiving end of said wedge nut said threaded cylindrical bore of said wedge nut such that rotation of said screw urges said wedge nut against said abutment transferring lateral force across said bearing surface.

16. Apparatus as defined in claim 15 wherein said abutment means comprises a unitary member having an insertion end adapted for insertion into said bore at a coronal end of said anchor means, said abutment having an internal bore and smooth outer walls at said insertion end terminating at an oblique bearing surface formed transversely of said internal bore at insertion end, and an attachment post extending beyond said coronal end for attachment of a prosthesis thereto.

17. Apparatus as defined in claim 16, wherein said lock means comprises a locking element disposed between said oblique bearing surface and said cylindrical wall and connected to said abutment means by a threaded member extending through said internal bore such that rotation of said threaded member urges said locking element axially within said axial bore in wedging engagement between said abutment and said cylindrical wall.

18. Apparatus as defined in claim 17 wherein said locking element is a wedge nut having a bearing surface formed obliquely to said threaded member for confronting engagement with said oblique bearing surface of said abutment means such that rotation of said threaded member urges said wedge nut against said oblique bearing surface such that a component of the force applied in rotation of said threaded member is transferred to urge said nut and insertion end laterally against said cylindrical walls.

19. Apparatus as defined in claim 18 wherein said threaded member has a laterally extending shoulder for engagement with a laterally extending seat formed in said internal bore.

20. Apparatus as defined in claim 19 wherein said wedge nut has a plurality of angularly space protrusions formed thereon for engagement in selected one of a plurality of indexing grooves formed in said wall of said axial bore.

21. An implant system for attaching a prosthesis to an osseous structure comprising:

a. an anchor to serve as a receptacle having a cylindrical smooth-walled axial bore with a terminal end and an entrant end;

b. an abutment having an insertion end for mating with said axial bore of said anchor, an internal cylindrical bore, and a coronal end, said insertion end having a bearing surface including at least one set of symmetrical protrusions, wherein said insertion end of said abutment further comprises two triangular symmetrical prongs having four bearing surfaces; and c. locking means engageable with said abutment for locking said abutment to said anchor by lateral expansion of said locking means, said locking means having four opposing bearing surfaces.

22. An implant system as in claim 21 wherein said locking means comprises a wedge nut cylindrically shaped having an insertion end, a superior end, and a threaded axial bore for receiving said abutment, the walls of said axial bore having symmetrically aligned triangular slits initiating at said superior end and terminating prior to the insertion end of said wedge nut for receiving said symmetrical prongs therein.

23. An implant system as in claim 22 wherein said cylindrical wedge nut is connected to said abutment with a threaded screw extending through said axial bore of said abutment engaging with said threaded axial bore of said wedge nut such that rotation of said screw urges said wedge nut against said abutment imparting a lateral force against said cylindrical axial bore of said anchor.

24. An implant system as described in claim 23 wherein said locking means comprises a locking element disposed between said bearing surface and said cylindrical wall and connected to said abutment by a threaded member extending through said axial bore of said abutment such that rotation of said threaded member urges said locking element axially within said cylindrical smooth-walled axial bore of said anchor.

25. An implant system as described in claim 24 wherein axial movement of said locking element against said abutment causes expansion of said locking element against said cylindrical smooth-walled axial bore.

\* \* \* \* \*